(12) United States Patent
Pacetti et al.

(10) Patent No.: US 8,562,669 B2
(45) Date of Patent: Oct. 22, 2013

(54) METHODS OF APPLICATION OF COATINGS COMPOSED OF HYDROPHOBIC, HIGH GLASS TRANSITION POLYMERS WITH TUNABLE DRUG RELEASE RATES

(75) Inventors: Stephen D. Pacetti, San Jose, CA (US); Gordon S. Stewart, San Francisco, CA (US); Victoria M. Gong, Sunnyvale, CA (US); Chandana Bellam, Sunnyvale, CA (US); Lisa M. Weldon, Mountain View, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1198 days.

(21) Appl. No.: 12/147,442

(22) Filed: Jun. 26, 2008

(65) Prior Publication Data

US 2009/0326645 A1  Dec. 31, 2009

(51) Int. Cl.
*A61F 2/82* (2013.01)
*A61K 9/52* (2006.01)

(52) U.S. Cl.
USPC .................................... 623/1.42; 427/2.21

(58) Field of Classification Search
USPC .............. 424/423; 525/413; 427/2.24, 2.25, 427/421.1, 424, 425, 427.3, 427.4, 427.5, 427/2.21; 623/1.42
See application file for complete search history.

(56) References Cited

U.S. PATENT DOCUMENTS

| | | | |
|---|---|---|---|
| 4,814,184 A | 3/1989 | Aguadisch et al. | |
| 6,096,726 A | 8/2000 | Opolski | |
| 6,153,252 A | 11/2000 | Hossainy et al. | |
| 6,191,100 B1 | 2/2001 | Askew et al. | |
| 6,265,016 B1 | 7/2001 | Hostettler et al. | |
| 6,368,658 B1 | 4/2002 | Schwarz et al. | |
| 6,524,274 B1 | 2/2003 | Rosenthal et al. | |
| 6,780,424 B2 | 8/2004 | Claude | |
| 6,896,965 B1 | 5/2005 | Hossainy | |
| 6,908,624 B2 | 6/2005 | Hossainy et al. | |
| 6,939,376 B2 | 9/2005 | Shulze et al. | |
| 7,087,263 B2 | 8/2006 | Hossainy et al. | |
| 7,094,256 B1 | 8/2006 | Shah et al. | |
| 7,166,680 B2 | 1/2007 | Desnoyer et al. | |
| 7,202,325 B2 | 4/2007 | Pacetti et al. | |
| 7,214,759 B2 | 5/2007 | Pacetti et al. | |
| 7,232,573 B1 | 6/2007 | Ding | |
| 7,244,443 B2 | 7/2007 | Pacetti | |
| 7,247,313 B2 | 7/2007 | Roorda et al. | |
| 7,261,946 B2 | 8/2007 | Claude | |
| 7,279,174 B2 | 10/2007 | Pacetti et al. | |
| 7,285,304 B1 | 10/2007 | Hossainy et al. | |
| 7,294,329 B1 | 11/2007 | Ding | |
| 7,318,932 B2 | 1/2008 | Pacetti | |
| 7,390,497 B2 | 6/2008 | Desnoyer et al. | |
| 7,419,504 B2 | 9/2008 | Hossainy | |
| 7,431,959 B1 | 10/2008 | Dehnad | |
| 7,438,722 B1 | 10/2008 | Hossainy | |
| 7,910,152 B2 | 3/2011 | Kleiner et al. | |
| 8,048,442 B1 | 11/2011 | Hossainy et al. | |
| 2003/0203000 A1 | 10/2003 | Schwarz et al. | |
| 2004/0030380 A1 | 2/2004 | Shulze et al. | |
| 2005/0112172 A1 | 5/2005 | Pacetti | |
| 2005/0208093 A1 | 9/2005 | Glauser et al. | |
| 2005/0244363 A1 | 11/2005 | Michal et al. | |
| 2005/0245637 A1 | 11/2005 | Tang et al. | |
| 2005/0265960 A1 | 12/2005 | Pacetti et al. | |
| 2005/0266038 A1 | 12/2005 | Glauser et al. | |
| 2005/0271700 A1 | 12/2005 | Desnoyer et al. | |
| 2005/0287184 A1 | 12/2005 | Hossainy et al. | |
| 2006/0002977 A1 | 1/2006 | Dugan | |
| 2006/0034888 A1 | 2/2006 | Pacetti et al. | |
| 2006/0067908 A1 | 3/2006 | Ding | |
| 2006/0089485 A1 | 4/2006 | Desnoyer et al. | |
| 2006/0115513 A1 | 6/2006 | Hossainy et al. | |
| 2006/0134165 A1 | 6/2006 | Pacetti | |
| 2006/0136048 A1 | 6/2006 | Pacetti et al. | |
| 2006/0182777 A1 | 8/2006 | Kangas | |
| 2006/0240065 A1 | 10/2006 | Chen | |
| 2006/0246108 A1 | 11/2006 | Pacetti et al. | |
| 2006/0246109 A1 | 11/2006 | Hossainy et al. | |
| 2006/0251721 A1* | 11/2006 | Cruz et al. | 424/468 |
| 2007/0003589 A1 | 1/2007 | Astafieva et al. | |
| 2007/0005130 A1 | 1/2007 | Glauser et al. | |
| 2007/0009565 A1 | 1/2007 | Pacetti et al. | |
| 2007/0026041 A1 | 2/2007 | Desnoyer et al. | |
| 2007/0032853 A1 | 2/2007 | Hossainy et al. | |
| 2007/0128246 A1 | 6/2007 | Hossainy et al. | |
| 2007/0135909 A1 | 6/2007 | Desnoyer | |
| 2007/0148251 A1 | 6/2007 | Hossainy et al. | |
| 2007/0202147 A1 | 8/2007 | Kleiner et al. | |

(Continued)

FOREIGN PATENT DOCUMENTS

WO WO 2007/146049  12/2007
WO WO 2007/146049 A2 * 12/2007
WO WO 2009/058666  5/2009

OTHER PUBLICATIONS

U.S. Appl. No. 09/956,521, filed Sep. 17, 2001, Hossainy et al.

(Continued)

*Primary Examiner* — Robert D. Harlan
(74) *Attorney, Agent, or Firm* — Squire Sanders (US) LLP (57) ABSTRACT

The present invention relates to methods of applying a drug—polymer coating layer onto an implantable medical device or another substrate, and the use of a choice of solvents to adjust the release of the drug from the coating. The drug to polymer ratio is about 1:1 to 1:3 on a mass basis. The polymer and the drug are hydrophobic.

23 Claims, 2 Drawing Sheets

(56) References Cited

U.S. PATENT DOCUMENTS

| | | |
|---|---|---|
| 2007/0202323 A1 | 8/2007 | Kleiner et al. |
| 2007/0207181 A1 | 9/2007 | Kleiner |
| 2007/0231363 A1 | 10/2007 | Chen et al. |
| 2007/0254107 A1 | 11/2007 | Rao et al. |
| 2007/0259101 A1 | 11/2007 | Hossainy et al. |
| 2007/0280988 A1 | 12/2007 | Ludwig et al. |
| 2007/0286882 A1 | 12/2007 | Tang et al. |
| 2007/0286885 A1 | 12/2007 | Hossainy et al. |
| 2007/0292495 A1 | 12/2007 | Ludwig et al. |
| 2007/0292518 A1 | 12/2007 | Ludwig |
| 2007/0293941 A1 | 12/2007 | Gale et al. |
| 2007/0298257 A1 | 12/2007 | Ludwig et al. |
| 2008/0003253 A1 | 1/2008 | Glauser |
| 2008/0095918 A1 | 4/2008 | Kleiner et al. |
| 2008/0124372 A1 | 5/2008 | Tang et al. |
| 2008/0160061 A1 | 7/2008 | Hossainy et al. |
| 2008/0305141 A1 | 12/2008 | Hossainy et al. |
| 2009/0053392 A1 | 2/2009 | Kramer-Brown et al. |
| 2009/0291111 A1 | 11/2009 | Lim et al. |
| 2011/0086162 A1 | 4/2011 | Hossainy et al. |
| 2011/0153004 A1 | 6/2011 | Kleiner et al. |
| 2011/0200660 A1 | 8/2011 | Kleiner et al. |

OTHER PUBLICATIONS

International Search Report for PCT/US2009/042749, mailed Aug. 5, 2010, 12 pgs.
U.S. Appl. No. 10/198,912, filed Jul. 19, 2002, Ding et al.
U.S. Appl. No. 10/316,739, filed Dec. 10, 2002, Zhang et al.
U.S. Appl. No. 10/376,348, filed Feb. 26, 2003, Ding et al.
U.S. Appl. No. 10/603,794, filed Jun. 25, 2003, Hossainy et al.
U.S. Appl. No. 10/723,137, filed Nov. 25, 2003, Claude et al.
U.S. Appl. No. 10/816,072, filed Mar. 31, 2004, Dugan et al.
U.S. Appl. No. 10/871,658, filed Jun. 18, 2004, Hossainy et al.
U.S. Appl. No. 10/909,795, filed Jun. 30, 2004, Ding et al.
U.S. Appl. No. 11/128,099, filed May 11, 2005, Manicka.
U.S. Appl. No. 11/187,467, filed Jul. 22, 2005, Desnoyer et al.
U.S. Appl. No. 11/437,075, filed May 18, 2006, Trollsas et al.
U.S. Appl. No. 11/450,558, filed Jun. 9, 2006, Tang et al.
U.S. Appl. No. 11/483,304, filed Jul. 6, 2006, Glauser.
U.S. Appl. No. 11/982,168, filed Oct. 31, 2007, Lim et al.
U.S. Appl. No. 11/982,160, filed Oct. 31, 2007, Lim et al.
U.S. Appl. No. 11/847,222, filed Aug. 29, 2007, Hsu et al.
Martin et al., "Enhancing the biological activity of immobilized osteopontin using a type-1 collagen affinity coating", J. of Biomedical Mat. Res. vol. 70, issue 1, pp. 10-19 (2004).
Spagnuolo et al., "Gas 1 is induced by VE-cadherin and vascular endothelial growth factor and inhibits endothelial cell apoptosis", Blood 103, pp. 3005-3012 (2003).
Völkel et al., "Targeting of immunoliposomes to endothelial cells using a single-chain Fv fragment directed against human endoglin (CD105)", Biochimica et Biophysica Acta 1663 pp. 158-166 (2004).
Cheung et al., "Covered metal stent for tumor obstruction of efferent loop recurrence after gastrectomy." *Surg Endosc* (1997) 11:936-938.
U.S. Appl. No. 10/807,546, filed Mar. 22, 2004, Hossainy et al.

\* cited by examiner

METHODS OF APPLICATION OF COATINGS COMPOSED OF HYDROPHOBIC, HIGH GLASS TRANSITION POLYMERS WITH TUNABLE DRUG RELEASE RATES

FIELD

This invention relates to the field of implantable medical devices (IMDs), more particularly to implantable medical devices having a coating from which drug(s) can be released at a target site in patient's body, and still more particularly to methods of coating the IMDs.

BACKGROUND

The discussion that follows is intended solely as background information to assist in the understanding of the invention herein; nothing in this section is intended to be, nor is it to be construed as, prior art to this invention.

Until the mid-1980s, the accepted treatment for atherosclerosis, i.e., narrowing of the coronary artery(ies) was coronary by-pass surgery. While effective and having evolved to a relatively high degree of safety for such an invasive procedure, by-pass surgery still involves serious potential complications and in the best of cases an extended recovery period.

With the advent of percutaneous transluminal coronary angioplasty (PTCA) in 1977, the scene changed dramatically. Using catheter techniques originally developed for heart exploration, inflatable balloons were employed to re-open occluded regions in arteries. The procedure was relatively non-invasive, took a very short time compared to by-pass surgery and the recovery time was minimal. However, PTCA brought with it another problem, elastic recoil of the stretched arterial wall which could undo much of what was accomplished and, in addition, failed to satisfactorily ameliorate another problem, restenosis, the re-clogging of the treated artery.

The next improvement, advanced in the mid-1980s was use of a stent to scaffold the vessel wall in place after PTCA. This for all intents and purposes put an end to recoil but did not entirely resolve the issue of restenosis. That is, prior to the introduction of stents, restenosis occurred in from 30-50% of patients undergoing PTCA. Stenting reduced this to about 15-20%, much improved, but still more than desirable.

In 2003, drug-eluting stents or DESs were introduced. The drugs initially employed with the DES were cytostatic compounds, compounds that curtailed the proliferation of cells that resulted in restenosis. The occurrence of restenosis was thereby reduced to about 5-7%, a relatively acceptable figure. Today, the DES is the default industry standard for the treatment of atherosclerosis and is rapidly gaining favor for treatment of stenoses of blood vessels other than coronary arteries such as peripheral angioplasty of the superficial femoral artery.

One of the key issues with DESs is control of the rate of release of the drug from the coating. If all of the drug is released soon after implantation, that is within a day or a few days, the intent of providing prolonged delivery is defeated. Furthermore, the drug levels may be toxic. On the other hand, drug delivery release rates which are too low may not provide a sufficiently high local concentration to have a therapeutic effect.

What is needed is a method of preparing a drug-releasing implantable medical device wherein drug(s) is(are) essentially homogenously dispersed in a drug reservoir layer so that it(they) can be released at a substantially consistent rate in vivo. The present invention provides such a method.

SUMMARY

Thus, an aspect of this invention is a method for modulation of the release of a hydrophobic drug from a hydrophobic coating. The method includes providing an amorphous or semi-crystalline hydrophobic polymer that has a glass transition temperature greater than 37° C., providing a hydrophobic drug, and providing a coating solvent including 100% acetone, or 10% to 90% acetone and 90% to 10% of a second solvent selected from the group consisting of methyl ethyl ketone, methyl isobutyl ketone and dimethylacetamide. The drug and the polymer are then dissolved in the coating solvent at a drug:polymer mass ratio in the range of about 1:1 to about 1:3 to form a coating solution. The coating solution is sprayed onto a substrate, and the solvent is removed.

In an aspect of this invention, the coating solvent includes 20% to 80% acetone and 80% to 20% of a second solvent selected from the group consisting of methyl ethyl ketone, methyl isobutyl ketone and dimethylacetamide.

In an aspect of this invention, the second solvent is methyl ethyl ketone.

In an aspect of this invention, the hydrophobic polymer is selected from the group consisting of poly(D,L-lactide), poly (L-lactide), poly(D,L-lactide-co-glycolide), poly(L-lactide-co-D,L-lactide), poly(L-lactide-co-glycolide) and combinations thereof.

In an aspect of this invention, the drug is a rapamycin derivative.

In an aspect of this invention, the drug is everolimus.

In an aspect of this invention, the drug is zotarolimus.

In an aspect of this invention, the coating thickness is less than about 50 µm.

An aspect of this invention is a method for modulation of hydrophobic drug release from a coating. The method includes providing an amorphous or semi-crystalline hydrophobic polymer that has a glass transition temperature greater than 37° C., providing a hydrophobic drug, and providing a first solvent that is a good solvent for both the polymer and the drug and has a boiling point less than or equal to 60° C. The drug and the polymer are dissolved in the first solvent at a drug:polymer mass ratio of about 1:1 to about 1:3 to form a first coating solution which is sprayed onto a substrate to form a first coating. The percent release of drug from the first coating over a selected time period is determined. A second solvent is provided that is a good solvent for both the polymer and the drug and has a boiling point that is at least 10° C. higher than the boiling point of the first solvent. The drug and the polymer are dissolved in the second solvent at the same drug:polymer mass ratio as that selected for the first solvent to form a second coating solution which is sprayed onto a substrate to form a second coating. The percent release of drug from the second coating over the same time period as that selected for release from the first coating is determined. A graph is prepared with percent drug release as the abscissa and percent of first solvent as the ordinate and the percent release at 100% first solvent and the percent release at 0% first solvent (100% second solvent) are plotted on the graph. A straight line is drawn between the two plotted points. A desired percent release over the selected time period is selected and the percent first and second solvent is determined from the graph.

In an aspect of this invention, the substrate that is coated is an implantable medical device.

In an aspect of this invention, the implantable medical device is a balloon catheter.

In an aspect of this invention is an implantable medical device with a coating applied according to an aspect of this invention.

In an aspect of this invention, the implantable medical device is a stent.

In an aspect of this invention, the stent further comprises a primer coating comprising 75/25 poly(D,L-lactide-co-glycolide).

DETAILED DESCRIPTION

DISCUSSION

Use of the singular herein includes the plural and visa versa unless expressly stated to be otherwise. That is, "a" and "the" refer to one or more of whatever the word modifies. For example, "a drug" may refer to one drug, two drugs, etc. Likewise, "the layer" may refer to one, two or more layers and "the polymer" may mean one polymer or a plurality of polymers. By the same token, words such as, without limitation, "layers" and "polymers" would refer to one layer or polymer as well as to a plurality of layers or polymers unless, again, it is expressly stated or obvious from the context that such is not intended.

As used herein, unless specified otherwise, any words of approximation such as, without limitation, "about," "essentially," "substantially" and the like mean that the element so modified need not be exactly what is described but can vary from the description by as much as ±15% without exceeding the scope of this invention.

As used herein, "optional" means that such item so modified may or may not be present.

The various embodiments of methods of applying a coating are applicable to those medical devices which could be used for drug delivery if coated with a coating by the one of the embodiments of the present invention. Particularly suitable medical devices include without limitation implantable medical devices.

As used herein, an "implantable medical device" refers to any type of appliance that is totally or partly introduced, surgically or medically, into a patient's body or by medical intervention into a natural orifice, and which is intended to remain there after the procedure. The duration of implantation may be essentially permanent, i.e., intended to remain in place for the remaining lifespan of the patient; until the device biodegrades; or until it is physically removed. Examples of implantable medical devices include, without limitation, implantable cardiac pacemakers and defibrillators; leads and electrodes for the preceding; implantable organ stimulators such as nerve, bladder, sphincter and diaphragm stimulators, cochlear implants; prostheses, vascular grafts, self-expandable stents, balloon-expandable stents, stent-grafts, grafts, artificial heart valves, foramen ovale closure devices, cerebrospinal fluid shunts, and intrauterine devices. An implantable medical device specifically designed and intended solely for the localized delivery of a therapeutic agent is within the scope of this invention.

As used herein with respect to an implantable medical device, "device body" refers to an implantable medical device in a fully formed utilitarian state with an outer surface to which no coating or layer of material different from that of which the device is manufactured has been applied. By "outer surface" is meant any surface however spatially oriented that is in contact with bodily tissue or fluids. A common example of a "device body" is a BMS, i.e., a bare metal stent, which, as the name implies, is a fully-formed usable stent that has not been coated with a layer of any material different from the metal of which it is made on any surface that is in contact with bodily tissue or fluids. Of course, device body refers not only to BMSs but to any uncoated device regardless of what it is made of. Implantable medical devices can be made of virtually any material including metals and/or polymers. The material from which the device is manufactured is not a limitation on the use of the coating methods of the present invention.

As used herein, a "polymer" is a molecule made up of the repetition of a simpler unit, herein referred to as a constitutional unit. The constitutional units themselves can be the product of the reactions of other compounds. A polymer may comprise one or more types of constitutional units. As used herein, the term polymer refers to a molecule comprising 2 or more constitutional units. Polymers may be straight or branched chain, star-like or dendritic, or one polymer may be attached (grafted) onto another. Polymers may have a random disposition of constitutional units along the chain, the constitutional units may be present as discrete blocks, or constitutional units may be so disposed as to form gradients of concentration along the polymer chain. Polymers may be cross-linked to form a network.

As used herein, "copolymer" refers to a polymer which includes more than one type of constitutional unit.

As used herein, "biocompatible" refers to a polymer or other material that both in its intact, that is, as synthesized, state and in its decomposed state, i.e., its degradation products, is not, or at least is minimally, toxic to living tissue; does not, or at least minimally and reparably, injure(s) living tissue; and/or does not, or at least minimally and/or controllably, cause(s) an immunological reaction in living tissue.

As used herein, the terms "biodegradable", "bioerodable", and "bioabsorbable" as well as degraded, eroded, absorbed, and dissolved, when used in reference to polymers, coatings, or other materials referenced herein, are used interchangeably, and refer to polymers, coatings, and materials that are capable of being completely or substantially completely, degraded, dissolved, and/or eroded over time when exposed to physiological conditions (pH, temperature, and fluid or other environment), and can be gradually resorbed, absorbed and/or eliminated by the body, or that can be degraded into fragments that can pass through the kidney membrane of an animal (e.g., a human). Conversely, a "biostable" polymer, coating, or material, refers to a polymer, coating or material that is not biodegradable.

As used herein "polyester" will refer to a substance "that meets the definition of polymer and whose polymer molecules contain at least two carboxylic acid ester linkages, at least one of which links internal monomer units together." (Adapted from 40 CFR 750.250(b))

As used herein, a "hydrophobic polymer" is one for which the water absorption by the polymer at 37° C. and normal atmospheric pressure, is not more than 5% by weight.

As used herein, a "hydrophobic drug" is one for which the solubility in water at 37° C., at normal atmospheric pressure, and at a pH in the range of 6.0 to 7.5, is less than 20 mg/ml.

As used herein, a "crosslink" refers to a joining of two separate chains of a polymer by reaction of non-terminal functional groups on the polymer with a multifunctional entity referred to as the cross-linking agent. As used herein, a "multifunctional crosslinking agent" is a compound having two or more functional groups that are capable of reacting with a functional group appended to the polymer backbone.

The glass transition temperatures, $T_g$, is the temperature at which a polymer (or a segment of a polymer) which is in an amorphous phase changes mechanical properties from those of a rubber (i.e., elastic) to those of a glass (brittle), when observations of material properties are made on the same time scale. The measured $T_g$ of a given polymer (or polymer segment) is dependent on the heating rate and is influenced by the thermal history, and potentially pressure history, of the polymer, as well as potentially the pressure at which the measurement is made. The chemical structure of the polymer heavily influences the glass transition by affecting chain mobility. Below the $T_g$ the polymeric molecules have very little rotational or translational freedom, i.e., they are unable to rotate or move easily or very far in relation to one another. Rather than moving around to adapt to an applied stress, they tend to separate violently so that the polymer breaks or shatters similarly to a pane of glass that is stressed. Above $T_g$, relatively facile segmental motion becomes possible and the polymer chains are able to move around and slip by one another such that when a stress is applied to the polymer it bends and flexes rather than breaks.

Plasticization of a polymer refers to the addition of a second, lower $T_g$ and generally lower molecular weight material, to a polymer. The effect is to lower the $T_g$ of the blend of the polymer and platiscizer, and generally, also to transform a hard, brittle material to a soft, rubber-like material. Not all lower $T_g$ materials will act as a plasticizer for a particular polymer. The two materials must be compatible and have some mutual solubility. Thus, the uptake of a plasticizer allows for greater polymer chain mobility, and as a result, a lower $T_g$.

As used herein, a material that is described as a layer or a film (e.g., a coating) "disposed over" an indicated substrate refers to, e.g., a coating of the material deposited directly or indirectly over at least a portion of the surface of the substrate. Direct depositing means that the coating is applied directly to the surface of the substrate. Indirect depositing means that the coating is applied to an intervening layer that has been deposited directly or indirectly over the substrate. A coating is supported by a surface of the substrate, whether the coating is deposited directly, or indirectly, onto the surface of the substrate. The terms "coating", "layer", and "coating layer" will be used interchangeably and refer to a layer, film, or coating as described in this paragraph. Unless the context clearly indicates otherwise, a reference to a coating, layer, or coating layer refers to a layer of material that covers all, or substantially all, of the outer surface, whether deposited directly or indirectly.

As used herein, a "primer layer" refers to a coating consisting of a polymer or blend of polymers that exhibit good adhesion characteristics with regard to the material of which the substrate is manufactured and whatever material is to be coated on the substrate. Thus, a primer layer serves as an adhesive intermediary layer between a substrate and materials to be carried by the device body and is, therefore, applied directly to the substrate.

As used herein, "drug reservoir layer" refers either to a layer of one or more drugs applied neat, or to a layer of polymer or blend of polymers that has dispersed within its three-dimensional structure one or more drugs. A polymeric drug reservoir layer is designed such that, by one mechanism or another, e.g., without limitation, by elution or as the result of biodegradation of the polymer, the drug is released from the layer into the surrounding environment. Preferred drug reservoir layers of the various aspects of the present invention are those including a drug and a polymer.

As used herein, "solvent" is defined as a substance capable of dissolving one or more substances or capable of at least partially dissolving the substance(s) to form a uniformly dispersed solution at the molecular- or ion-size level at a selected temperature and pressure. A solvent can refer to one chemical compound, or a mixture of chemical compounds. A solvent can be a fluid.

As used herein a "good solvent for a drug" is one in which the solubility, at the temperature or pressure selected, is at least 20 mg/ml. As used herein a "good solvent for a polymer" is one in which the solubility, at the temperature and pressure selected, is at least 50 mg/ml.

As used herein, "therapeutic agent," "drug" or "active agent," which will be used interchangeably, refers to any substance that, when administered in a therapeutically effective amount to a patient suffering from a disease or condition, has a therapeutic beneficial effect on the health and well-being of the patient. A therapeutic beneficial effect on the health and well-being of an individual includes, but is not limited to: (1) curing the disease or condition; (2) slowing the progress of the disease or condition; (3) causing the disease or condition to retrogress; or, (4) alleviating one or more symptoms of the disease or condition.

As used herein, a drug also includes any substance that when administered to a patient, known or suspected of being particularly susceptible to a disease, in a prophylactically effective amount, has a prophylactic beneficial effect on the health and well-being of the patient. A prophylactic beneficial effect on the health and well-being of a patient includes, but is not limited to: (1) preventing or delaying on-set of the disease or condition in the first place; (2) maintaining a disease or condition at a retrogressed level once such level has been achieved by a therapeutically effective amount of a substance, which may be the same as or different from the substance used in a prophylactically effective amount; or, (3) preventing or delaying recurrence of the disease or condition after a course of treatment with a therapeutically effective amount of a substance, which may be the same as or different from the substance used in a prophylactically effective amount, has concluded.

As used herein, "therapeutic agent," "drug," "active agent," and "biologically active agent" also refers to pharmaceutically acceptable, pharmacologically active derivatives of those drugs specifically mentioned herein, including, but not limited to, salts, esters, amides, prodrugs, active metabolites, analogs, and the like.

As used herein, "release rate" refers to the speed of drug release from a drug delivery system or formulation per unit of time, for example without limitation 0.1 mg per hour (0.1 mg/hr) or 100 mg per day. The preferred drug delivery systems or formulations of the present invention are coatings for implantable medical devices that include one or more drugs.

As used herein, "release duration," refers to the total time over which a drug is released in a therapeutically effective amount from a drug delivery system or formulation. Thus, for example without limitation, a drug release range of, say, 1 hour to 72 hours means that a therapeutically effective amount of the drug is released over that time period.

As used herein, "cumulative drug release" refers to the total amount of drug released from the drug delivery system or formulation up to a given point in time, such as, without limitation, 24 hours. The "cumulative drug release" is usually expressed as a percent of the total content (total drug content) of the drug delivery system or formulation. In such a calculation, the total content that is used in the denominator may be obtained from actual measurements (analytical assay of a number of units), theoretical (for example gravimetric weight gain of a coating and the % drug as a % solids in the coating solution), or label claim.

As used herein, "substantially released" refers to a cumulative release of the drug of about 80% or more.

As used herein, any measurement of drug release, for example without limitation, release rate, release duration, or substantially released, refers to the an in-vitro measurement using a United States Pharmacopeia Type VII apparatus, using porcine serum with sodium azide optionally added (0.1% w/v) at a temperature of 37° C.

The "percolation threshold" is the point at which domains of one phase in a multiple phase system begins to connect and form an interconnected network of the phase within the multiple phase system. The percolation threshold is the point at which the one phase can form its own channels for diffusion through interconnected domains. Percolation thresholds are generally expressed as a volume fraction and are a function of the domain size and shape for each of the phases in the multiple phase system.

Although the explanation that follows will utilize a stent as an exemplary embodiment of a substrate for coating, the various aspects of the present invention are not limited to stents.

As outlined above, control of the drug release rate from a DES is important. In many cases, a DES is fabricated by coating a stent, as a non-limiting example, a bare-metal stent, with a coating containing a drug. The coating typically contains one or more polymers that control the release of the drug from the coating.

The typical manufacturing process for coating a stent is dissolving or dispersing a polymer, optionally with other additives, and a drug, in a solvent, and disposing the resulting coating solution over the stent by procedures such as spraying or immersing the stent in the solution. Such coating procedures are well-known in the art.

After the solution has been disposed over the stent, the solvent is removed, or substantially removed, by evaporation. When the solvent is removed, what is left is the solid material which forms a layer, film, or coating on the surface of the implantable medical device, either directly or indirectly. The solid material left, polymer and optionally other materials, is referred to as the % solids in the solution. The process of drying can be accelerated if the drying is conducted at an elevated temperature, and/or with the addition of a flow of air (or another gas or fluid) over or past the device to enhance mass transfer of the solvent. The coating layer left may include residual solvents as removal of absolutely all of the solvent is generally not possible.

Figure 1:
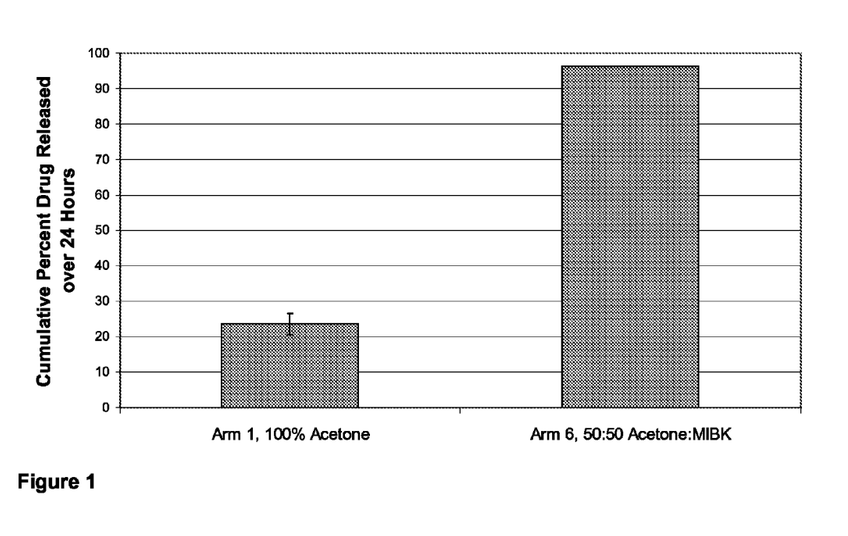
FIG. 1 depicts the cumulative release of everolimus over 24 hours from coated stents in which the drug to polymer ratio in the coating is 1:1.

Various aspects of the present invention relate to methods of applying a coating including drug and polymer onto a substrate. Surprisingly, it has been found that the cumulative drug release at 24 hours of everolimus from a stent coating of everolimus and 75:25 poly (D,L lactide-co-glycolide) (PLGA, where the 75:25 refers to the molar ratio of the D,L-lactide and glycolide constitutional units, respectively, in the polymer) at a mass (or weight) ratio of drug to polymer of 1:1 differed if the coating was applied to the stent by spraying the drug and polymer from a solution of 100% acetone rather than from a solution of 50:50 (w/w) acetone:methyl isobutyl ketone. The cumulative release at 24 hours for the stent coated from a solution of acetone was about 23% while about 96% for the stent coated from the solution made with 50:50 acetone:methyl isobutyl ketone. The coating experiment is described in Example 1 and data are illustrated in FIG. 1. Acetone has a boiling point of 56° C., while methyl isobutyl ketone is 116.5° C.

Without being bound by theory, it is believed that the coating applied by spraying a solution made with acetone, which quickly evaporates, results in a coating with a different microstructure than the coating applied by spraying a solution made with acetone and methyl isobutyl ketone. Specifically, it is believed that the slower evaporating solvent (methyl isobutyl ketone) allows more time for phase separation between the drug and polymer, and thus the drug forms larger drug-rich domains. The drug may also have time to migrate to the surface where it is immediately exposed to fluid after implantation (or in an in-vitro experiment). The larger domains increase the likelihood that the drug is present as an interconnected discontinuous phase, which may co-exist with a continuous polymer-rich phase. In other words, the drug exists at or above its percolation threshold in the coating. When drug is present as a connected discontinuous phase, the dissolving drug creates channels for additional drug release via diffusion through the channels. It is expected that the diffusion of the drug through the fluid filled channel as the drug dissolves creates a tortuous channel for additional drug release. Thus, it is believed that the drug release is faster if the drug diffuses through the fluid-filled channels than if the drug were to diffuse through the polymer matrix.

Without being bound by theory, it is believed that the rapid evaporation of the acetone leaves little time for phase separation, and thus leads to smaller domains of the drug, and potentially, some of the drug is in the polymer rich phase as well. As the drug exists as smaller domains size, the pores remaining after drug dissolution are smaller. Also, as the size of the drug domains becomes smaller the percolation threshold tends to be increased. In the limit of extremely fast solvent evaporation, the drug is kinetically frozen in the polymer matrix and a largely amorphous phase results. Thus a pseudo-steady-state solid solution of polymer and amorphous drug may be formed where the drug is distributed on a smaller, and potentially, molecular scale. In addition, quick evaporation of the solvent not only precipitates the polymer and drug rapidly, but it could induce the formation of a polymer rich skin on the coating. A polymer-rich skin can act as a membrane to slow drug release. Without being bound by theory, it is also believed that the choice of solvent, and its solvency for the drug and polymer, has an influence on the coating microstructure. In particular, dimethyl acetamide, a solvent with a boiling point of 165° C. was used in a 50:50 (w/w) blend with acetone for the application of a stent coating of everolimus and 75:25 poly (D,L lactide-co-glycolide) at a weight ratio of drug to polymer of 1:2. The cumulative release at 24 hours from the stent coating made by spraying a solution made from the 50:50 blend of acetone and dimethyl acetamide was about 42% while the coating made by spraying from 50:50 blend of acetone and methyl isobutyl ketone was about 83% (see Example 2 and FIG. 3 below). Dimethyl acetamide is a good solvent for the polymer and a very good solvent for the drug.

Thus, the ability of this second, trailing solvent to keep the drug and polymer in solution ameliorates the impact of the slow evaporation due to the high boiling point.

The various aspects of the present invention include a method of modulating the cumulative release of drug from a coating applied by spray coating a substrate, such as a stent, by choosing a particular solvent or a solvent mixture. The various aspects of the present invention apply to coatings wherein the polymer is semi-crystalline or amorphous, hydrophobic, and has a glass transition temperature of greater than 37° C. Because the polymer has a glass transition temperature greater than 37° C., the polymer in the coating is in a glassy or brittle state when implanted, for example without limitation, in a human body.

As used herein the glass transition temperature of the polymer will refer to the glass transition temperature of the polymer in an unplasticized state (not more than 0.5% by weight water, and total volatile organic carbon level less than 1000 ppm) as measured by standard differential scanning calorimetry (modulated or unmodulated) with a temperature ramp of 5-40° C./min and if modulated, with a temperature modulation of 0.01 to 10° C. with a modulation period of 1 to 100 seconds, utilizing nitrogen or argon at a flow rate of 20-200 ml/min.

In the various aspects of this invention, the drug may be hydrophobic.

In the various aspects of the present invention, the drug to polymer ratio in the coating ranges from about 1:1 to about 1:3 on a mass basis. In some aspects the drug to polymer ratio is one in which the drug is not soluble in the polymer at equilibrium.

The various aspects of the present invention involve the choice of solvent, or solvent mixture, from which a coating is applied to modulate the release rate of the drug from the coating. The solvent or solvent mixture will be referred to as the coating solvent. Measurement of the release rate can be, for example without limitation, determined by measuring the cumulative release at 24 hours. Thus one solvent is chosen that quickly evaporates while a second solvent is chosen with a higher boiling point, and therefore evaporates more slowly than the first solvent. By varying the ratio of the two solvents in the coating solvent the release rate can be tuned.

In the various aspects of the present invention a first solvent is chosen that is a good solvent for both the polymer and the drug. The first solvent may have a boiling point of about 60° C. or less. In some aspects of the invention, the first solvent may have a boiling point of about 56° C. or less. In some aspects of the invention, the first solvent may have a boiling point of about 50° C. or less.

In the various aspects of the invention, a second solvent is chosen is a good solvent for both the polymer and the drug. In addition, the second solvent has a boiling point different from that of the first solvent. In some aspects of the invention, the difference is at least about 10° C., at least about 15° C., at least about 20° C., or at least about 25° C. higher than the boiling point of the first solvent. In some aspects of the present invention, the second solvent may have a boiling point that is between 60° C. and 210° C., or more preferably between 70° C. and 170° C.

In some aspects of the present invention, the second solvent may be a better solvent for the drug than for the polymer, while in other aspects of the present invention the second solvent may be a better solvent for the polymer than the drug. In some aspects of the present invention, the first solvent may be a better solvent for the drug than for the polymer, while in other aspects the first solvent may be a better solvent for the polymer than the drug.

Although the second solvent is a good solvent for both the polymer and the drug, it is preferable that the second solvent is a better solvent for the drug than for the polymer. Without being bound by theory, it is believed that with respect to the second solvent, which evaporates slower than the first solvent, keeping the drug in solution longer than the polymer may reduce release rate as the polymer effectively partitions or precipitates to the exterior of a droplet of coating solution, resulting in a type of "microencapsulation" of the drug as the coating solvent is removed. In effect, the microstructure that results is analogous to a closed cell foam in which the air space is occupied by drug, and the cell walls are composed of polymer. Thus, the drug particles are effectively prevented from touching each other, and are not able to form as many interconnected pores.

As used herein, the % solvent in the solvent mixtures that form a coating solvent is measured by the weight or mass of each solvent that is added to form the mixture. The first and second solvents may be of a very high purity grade such as HPLC grade, United States Pharmacopeia, National Formulary, Food Compendium Codex grade, American Chemical Society (ACS) reagent grade, or any other suitable grade. However, in some aspects of the present inventions, it is important that the grade of any of the solvents used be anhydrous, or alternatively, have a water content, measured on a mass basis, of not more than 0.5% (w/w).

In the various aspects of the present invention, the coating solvent may include 100% acetone, or 10%-90% acetone and 90%-10% of the second solvent, preferably 20%-80% acetone and 80%-20% of the second solvent, subject to the limitation that the two solvent percentages sum to 100%. In some aspects, either the first and/or the second solvent may itself be a mixture of solvents.

As used herein, a "coating solvent" which consists of only one solvent, such as for example without limitation ACS reagent grade acetone, will be referred to as 100% acetone despite the fact that the acetone, as received, contains some impurities, and/or the actual acetone assay is less than 100% on a molar, volume, mass or other basis. Similarly, a "coating solvent" of two solvents, will be referred to as a mixture of the two solvents such that the percent of the two solvents sum to 100% despite the presence of some impurities in each of the solvents.

For the various aspects of the present invention, the coating solution formed by dissolving the polymer and the drug in the coating solvent is a true solution as opposed to a dispersion. In some aspects of the present invention, the coating solution may be heated to a temperature that is higher than the ambient temperature, such as without limitation, 35° C. or 40° C.

The various aspects of the present invention produce a coating with a thickness from 0.2 microns to 50 microns, preferably 0.5 microns to 25 microns, and more preferably 1 micron to 15 microns.

The various aspects of the present invention may be used to apply a coating to an implantable medical device, such as a stent, either directly, or indirectly, that is on top of another coating. In the various aspects of the invention the methods may be used to spray coat a drug reservoir coating onto an implantable medical device that has a primer coating. In the various aspects, an additional coating may be applied on top of the drug reservoir coating, and/or there may be any number of additional coatings between the primer layer and the drug reservoir coating. In some aspects of the present invention, the methods may be used to apply more than one drug reservoir layer to a device. Preferred embodiments include a primer coating without a coating on top of the drug reservoir coating.

In some aspects of the present invention, the coating may cover all, or substantially all, of the surface of the substrate, such as an implantable medical device. As a non-limiting example, for an implantable medical device such as a stent, all or substantially all of the outer surface of the device body or the device may be coated. In some aspects of the present invention, the coating may cover only part of or portions of the substrate. In some aspects of the present invention, the coating may be selectively applied to certain portions of the substrate.

In some aspects of the present invention, application of the coating solution to the stent to form a coating is accomplished by spraying a solution onto the stent, the solution being atomized with compressed air, nitrogen, argon, or other inert gas (or another compressed gas or a supercritical fluid). Important aspects of the spray coating process include the pressure of the atomizing gas and the spray nozzle to part distance. Working ranges for the atomizing gas pressure and spray nozzle to part distance process parameters are 1 to 50 psi, and 1 to 40 mm, respectively. Preferred ranges are 2 to 30 psi and 2 to 25 mm, respectively. The most preferred ranges are 5 to 20 psi and 5 to 20 mm, respectively.

Representative substrates onto which a coating is applied utilizing various aspects of the present invention include any substrate for which a coating is beneficial or desirable. Preferred substrates are medical devices including implantable medical devices, such as without limitation stents, as well as devices which are inserted into the body for limited time periods such as without limitation during a medical procedure. Non-limiting examples of devices with a short-term exposure include catheters, catheter balloons, contact lenses, and the like.

Representative examples of polymers that may be used in the various embodiments of the present invention include without limitation poly(3-hydroxyvalerate), poly(lactide-co-glycolide), poly(3-hydroxybutyrate), poly(4-hydroxybutyrate), poly(3-hydroxybutyrate-co-3-hydroxyvalerate), polyorthoesters, polyanhydrides, poly(glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly(glycolide-co-caprolactone), poly(trimethylene carbonate), polyester amides, poly(glycolic acid-co-trimethylene carbonate), polyphosphazenes, polyesters, polyolefins, polyisobutylene and ethylene-alphaolefin copolymers, acrylic polymers and copolymers, vinyl halide polymers and copolymers (such as polyvinyl chloride), polyvinyl ethers (such as polyvinyl methyl ether), polyvinylidene halides (such as polyvinylidene chloride), polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose acetate, cellulose butyrate, cellulose acetate butyrate, cellophane, cellulose nitrate, cellulose propionate, cellulose ethers, and ethylene vinyl alcohol copolymer (commonly known by the generic name EVOH or by the trade name EVAL™), poly(butyl methacrylate), poly(vinylidene fluoride-co-hexafluoropropene) (e.g., SOLEF 21508™, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, poly(vinyl acetate), styrene-isobutylene-styrene triblock copolymers, and combinations thereof.

A preferred list of polymers are biodegradable polyesters, specifically including poly(D,L-lactide), poly(L-lactide), poly(D,L-lactide-co-glycolide), poly(L-lactide-co-D,L-lactide), poly(L-lactide-co-glycolide), and combinations thereof.

Biologically Active Agents

In some embodiments, the implantable device described herein can optionally include at least one biologically active ("bioactive") agent. The at least one bioactive agent can include any substance capable of exerting a therapeutic, prophylactic or diagnostic effect for a patient.

Examples of suitable bioactive agents include, but are not limited to, synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules that bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. The bioactive agents could be designed, e.g., to inhibit the activity of vascular smooth muscle cells. They could be directed at inhibiting abnormal or inappropriate migration and/or proliferation of smooth muscle cells to inhibit restenosis.

In certain embodiments, optionally in combination with one or more other embodiments described herein, the implantable device can include at least one biologically active agent selected from antiproliferative, antineoplastic, antimitotic, anti-inflammatory, antiplatelet, anticoagulant, antifibrin, antithrombin, antibiotic, antiallergic and antioxidant substances.

A preferred class of drugs is the class of antiproliferative drugs. Examples of antiproliferative drugs include, without limitation, actinomycins, taxol, docetaxel, paclitaxel, rapamycin, 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin, zotarolimus, ABT-578, everolimus, biolimus A9 (Biosensors International, Singapore), deforolimus, AP23572 (Ariad Pharmaceuticals), tacrolimus, zotarolimus, pimecrolimus, temsirolimus, and perfenidone.

Another preferred class of drugs is the class of anti-inflammatory drugs. Examples of anti-inflammatory drugs include both steroidal and non-steroidal (NSAID) anti-inflammatories such as, without limitation, clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone, dexamethasone dipropionate, dexamethasone acetate, dexmethasone phosphate, momentasone, cortisone, cortisone acetate, hydrocortisone, prednisone, prednisone acetate, betamethasone, betamethasone acetate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus and pimecrolimus.

In addition, the bioactive agents can be other than antiproliferative or anti-inflammatory agents. The bioactive agents can be any agent that is a therapeutic, prophylactic or diagnostic agent. In some embodiments, such agents can be used in combination with antiproliferative or anti-inflammatory agents. These bioactive agents can also have antiproliferative and/or anti-inflammatory properties or can have other properties such as antineoplastic, antimitotic, cystostatic, antiplatelet, anticoagulant, antifibrin, antithrombin, antibiotic, antiallergic, and/or antioxidant properties.

Examples of antineoplastics and/or antimitotics include, but are not limited to, paclitaxel (e.g., TAXOL® available from Bristol-Myers Squibb), docetaxel (e.g., TAXOTERE® from Aventis), methotrexate, azathioprine, vincristine, vinblastine, fluorouracil, doxorubicin hydrochloride (e.g., ADRIAMYCIN® from Pfizer), and mitomycin (e.g., MUTAMYCIN® from Bristol-Myers Squibb).

Examples of antiplatelet, anticoagulant, antifibrin, and antithrombin agents that can also have cytostatic or antiproliferative properties include, but are not limited to, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as ANGIOMAX® (from Biogen), calcium channel blockers (e.g., nifedipine), colchicine, fibroblast growth factor (FGF) antagonists, fish oil (e.g., omega 3-fatty acid), histamine antagonists, lovastatin (a cholesterol-lowering drug that inhibits HMG-CoA reductase, brand name MEVACOR® from Merck), monoclonal antibodies (e.g., those specific for platelet-derived growth factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetics, 4-amino-2,2,6,6-tetramethylpiperidine-1-oxyl (4-amino-TEMPO), estradiol, anticancer agents, dietary supplements such as various vitamins, and a combination thereof.

Examples of cytostatic substances include, but are not limited to, angiopeptin, angiotensin converting enzyme inhibitors such as captopril (e.g., CAPOTEN™ and CAPOZIDE™ from Bristol-Myers Squibb), cilazapril and lisinopril (e.g., PRINIVIL® and PRINZIDE® from Merck).

Examples of antiallergic agents include, but are not limited to, permirolast potassium. Examples of antioxidant substances include, but are not limited to, 4-amino-2,2,6,6-tetramethylpiperidine-1-oxyl (4-amino-TEMPO). Other bioactive agents include anti-infectives such as antiviral agents; analgesics and analgesic combinations; anorexics; antihelmintics; antiarthritics, antiasthmatic agents; anticonvulsants; antidepressants; antidiuretic agents; antidiarrheals; antihistamines; antimigrain preparations; antinauseants; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary vasodilators; peripheral and cerebral vasodilators; central nervous system stimulants; cough and cold preparations, including decongestants; hypnotics; immunosuppressives; muscle relaxants; parasympatholytics; psychostimulants; sedatives; tranquilizers; naturally derived or genetically engineered lipoproteins; and restenoic reducing agents.

Other biologically active agents that can be used include alpha-interferon, genetically engineered epithelial cells, tacrolimus and dexamethasone.

A "prohealing" drug or agent, in the context of a blood-contacting implantable device, refers to a drug or agent that has the property that it promotes or enhances re-endothelialization of arterial lumen to promote healing of the vascular tissue. The portion(s) of an implantable device (e.g., a stent) containing a prohealing drug or agent can attract, bind and eventually become encapsulated by endothelial cells (e.g., endothelial progenitor cells). The attraction, binding, and encapsulation of the cells will reduce or prevent the formation of emboli or thrombi due to the loss of the mechanical properties that could occur if the stent was insufficiently encapsulated. The enhanced re-endothelialization can promote the endothelialization at a rate faster than the loss of mechanical properties of the stent.

The prohealing drug or agent can be dispersed in the body of the bioabsorbable polymer substrate or scaffolding. The prohealing drug or agent can also be dispersed within a bioabsorbable polymer coating over a surface of an implantable device (e.g., a stent).

"Endothelial progenitor cells" refer to primitive cells made in the bone marrow that can enter the bloodstream and go to areas of blood vessel injury to help repair the damage. Endothelial progenitor cells circulate in adult human peripheral blood and are mobilized from bone marrow by cytokines, growth factors, and ischemic conditions. Vascular injury is repaired by both angiogenesis and vasculogenesis mechanisms. Circulating endothelial progenitor cells contribute to repair of injured blood vessels mainly via a vasculogenesis mechanism.

In some embodiments, the prohealing drug or agent can be an endothelial cell (EDC)-binding agent. In certain embodiments, the EDC-binding agent can be a protein, peptide or antibody, which can be, e.g., one of collagen type 1, a 23 peptide fragment known as single chain Fv fragment (scFv A5), a junction membrane protein vascular endothelial (VE)- cadherin, and combinations thereof. Collagen type 1, when bound to osteopontin, has been shown to promote adhesion of endothelial cells and modulate their viability by the down regulation of apoptotic pathways. S. M. Martin, et al., *J. Biomed. Mater. Res.,* 70A:10-19 (2004). Endothelial cells can be selectively targeted (for the targeted delivery of immunoliposomes) using scFv A5. T. Volkel, et al., *Biochimica et Biophysica Acta,* 1663:158-166 (2004). Junction membrane protein vascular endothelial (VE)-cadherin has been shown to bind to endothelial cells and down regulate apoptosis of the endothelial cells. R. Spagnuolo, et al., *Blood,* 103:3005-3012 (2004).

In a particular embodiment, the EDC-binding agent can be the active fragment of osteopontin, (Asp-Val-Asp-Val-Pro-Asp-Gly-Asp-Ser-Leu-Ala-Try-Gly). Other EDC-binding agents include, but are not limited to, EPC (epithelial cell) antibodies, RGD peptide sequences, RGD mimetics, and combinations thereof.

In further embodiments, the prohealing drug or agent can be a substance or agent that attracts and binds endothelial progenitor cells. Representative substances or agents that attract and bind endothelial progenitor cells include antibodies such as CD-34, CD-133 and vegf type 2 receptor. An agent that attracts and binds endothelial progenitor cells can include a polymer having nitric oxide donor groups.

Some exemplary, but not-limiting solvents, for use in the present invention include, but are not limited to, dimethyl acetamide (DMAC), dimethyl formamide (DMF), tetrahydrofuran (THF), TCE (1,1,2,2-tetrachloroethane), acetone, Dowanol™ (2-(2-ethoxyethoxy)ethanol), DCM (dichloromethane), MEK (methyl ethyl ketone), MIBK (methyl isobutyl ketone), chloroform, ethanol, butanol, isopropyl acetate, pentane, cyclohexanone, xylene, toluene, propylene glycol monomethyl ether, methyl butyl ketone, ethyl acetate, n-butyl acetate, and dioxane.

A list of preferred solvents includes acetone, methyl ethyl ketone, methyl isobutyl ketone and dimethylacetamide.

EXAMPLES

The examples presented in this section are provided by way of illustration of the current invention only and are not intended nor are they to be construed as limiting the scope of this invention in any manner whatsoever. Each of the examples the follows relates to the coating of 3 mm×12 mm VISION (Abbott Cardiovascular Systems Inc.) stent, which has a coatable surface area of 0.5556 cm².

Example 1

All stents were cleaned by being sonicated in isopropyl alcohol. Stents were coated with a primer layer of approximately 51 μg of 75:25 PLGA (poly(D,L-lactide-co-glycolide) provided by Boehringer Ingelheim, grade RG755S) by spraying from a solution of 2 weight % polymer in 90:10 acetone:methyl isobutyl ketone (w/w). More than one pass under the coater was required to obtain the target weight of polymer on the stent. The spraying operation was carried out with a custom made spray coater equipped with a spray nozzle, a drying nozzle, and a means to rotate and translate the stent under the nozzles with the processing parameters outlined in Table 1. Subsequent to coating, all stents were baked in a forced air convection oven at 140° C. for 30 minutes. After removal from the oven and weighing, the stents were coated with a solution of 75:25 PLGA and everolimus (supplied by Novartis) with a drug to polymer ratio of 1:1 (w/w) in solvent (4 weight % total solids). More than one pass under the coater was required to obtain the target weight of polymer on the stent. The spraying operation was carried out with the same coater used for the primer spraying with the following parameters outlined in Table 2. After the drug layer coating, the stents were baked in a force air convection oven at 50° C. for 1 hour. After baking the coating, the stents were crimped onto 3.0×12 mm XIENCE V catheters, placed in protective tubular coils, and then sealed in Argon filled foil pouches. The stents were not sterilized. Cumulative release of the drug everolimus at 24 hours was determined using a United States Pharmacopeia type 7 tester in porcine serum with sodium azide 0.1% (w/v) added as the dissolution media. Everolimus released into solution was determined by HPLC analysis on the amount of drug remaining on the stent. The cumulative release expressed is one minus the fractional amount of drug remaining divided by the theoretical quantity or dose of drug per stent. In this experiment, the same drug to polymer ratio and the same polymer and drug were used but the spray coating was accomplished with different solvents. In one set of stents, the solvent was 100% acetone while for other stents the solvent was a 50:50 (w/w) mixture of acetone and methyl isobutyl ketone. The cumulative release as measured of drug after 24 hours for n=3 stents is illustrated in FIG. 1.

TABLE 1

Spray Processing Parameters Primer Layer Coating

| Primer Spray Head | |
|---|---|
| Spray nozzle to stent distance (mm) | 12 ± 1 |
| Solution flow rate | 3.2 ml/hr |
| Atomization pressure (psi) | 12.5 ± 0.5 |
| Dry Heat Nozzle | |
| Drying nozzle temp (° C.) | 50 |
| Drying nozzle pressure (psi) | 15 ± 2 |
| Spray nozzle to stent distance (mm) | 12 ± 1 |
| Flow Rate and Coating Weight | |
| Target Flow Rate in ug/pass | 8-9 |
| Target Weight (μg) | 51 |

TABLE 2

Spray Processing Parameters Drug Layer Coating

| Drug Layer Spray Head | |
|---|---|
| Spray nozzle to mandrel distance (mm) | 12 ± 1 |
| Solution flow rate | 2.2-2.5 ml/hr |
| Atomization pressure (psi) | 15 ± 2.5 |
| Air Dry Heat Nozzle | |
| Drying nozzle temp (° C.) | 50 |
| Drying nozzle pressure (psi) | 15 ± 2 |
| Spray nozzle to mandrel dist (mm) | 12 ± 1 |
| Flow Rate and Coating Weight | |
| Target Flow Rate in μg/pass | 14-15 |
| Target Weight (μg) | 112 |

Example 2

Figure 2:
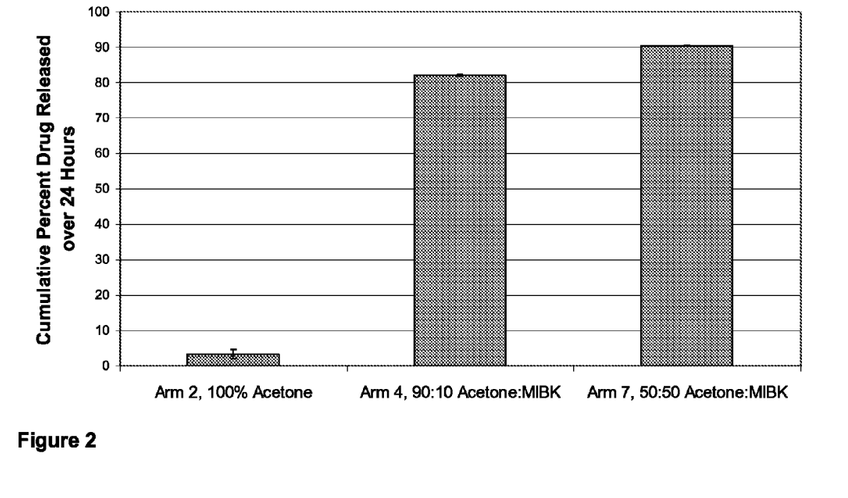
FIG. 2 depicts the cumulative release of everolimus over 24 hours from coated stents in which the drug to polymer ratio in the coating is 1:2.

Stents were cleaned, coated with a primer of 75/25 PLGA, and then coated with a drug layer as described in Example 1 except that the drug to polymer ratio was 1:2 (and therefore the % solids in the coating solution was 3% (w/w)). The solvents utilized for the drug layer coating were all acetone, 50:50 acetone:methyl isobutyl ketone, and 90:10 acetone: methyl isobutyl ketone. As in example 1, the ratios refer to the weight of each solvent added to form the mixture. FIG. 2 illustrates the cumulative release in porcine serum after 24 hours for n=3 stents from the different coating solvents.

Example 3

Figure 3:
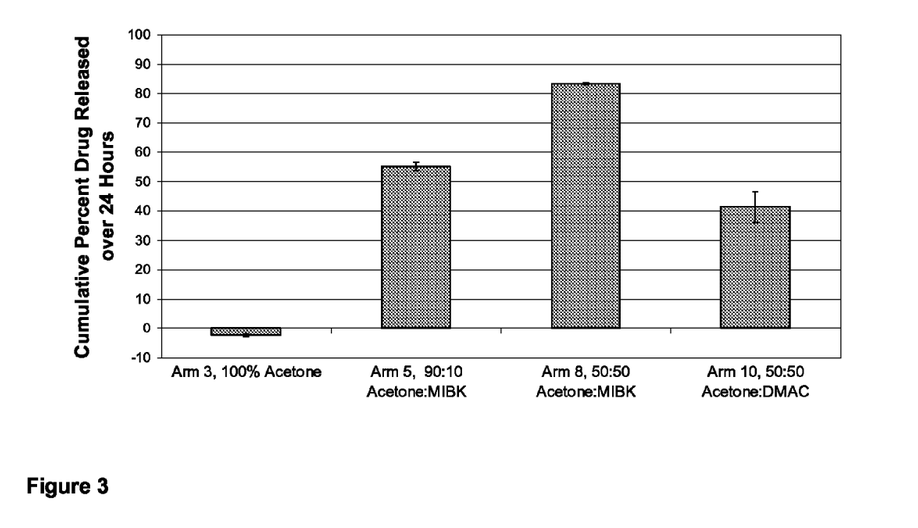
FIG. 3 depicts the cumulative release of everolimus over 24 hours from coated stents in which the drug to polymer ratio in the coating is 1:3.

Stents were cleaned, coated with a primer of 75/25 PLGA, and then coated with a drug layer as described in Example 1 except that the drug to polymer ratio was 1:3 (and therefore the % solids in the coating solution was 2.75%). The solvents utilized for the drug layer coating were all acetone, 50:50 acetone:methyl isobutyl ketone, 90:10 acetone:methyl isobutyl ketone, and 50:50 acetone:dimethyl acetamide. As in example 1, the ratios refer to the weight of each solvent added to form the mixture. FIG. 3 illustrates the cumulative release in porcine serum after 24 hours.

Example 4

Figure 4:
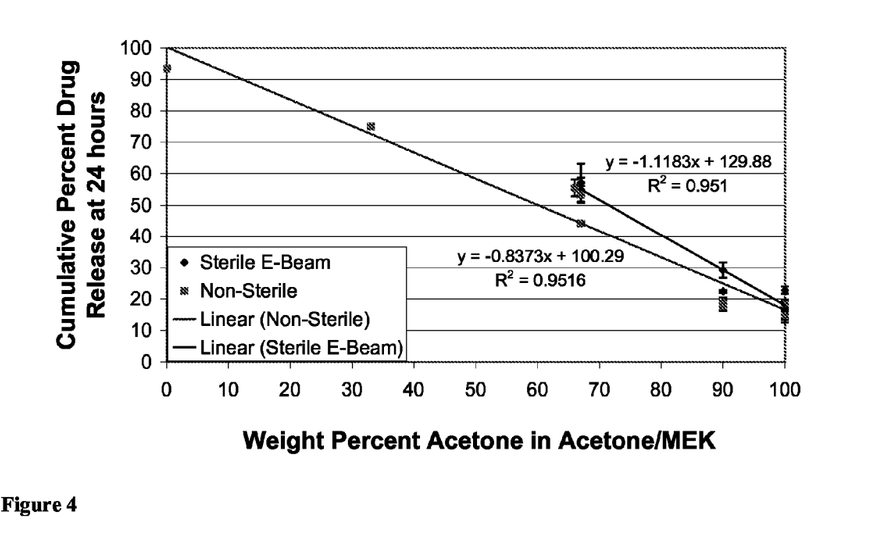
FIG. 4 graphically depicts the cumulative percentage everolimus released by a stent with a coating as a function of the percent of acetone in the coating solvent, a mixture of acetone and methylethyl ketone.

In a number of separate studies, stents were cleaned, coated with a primer of 75/25 PLGA, and then coated with a drug layer as described in Example 1. As in Example 1, the drug to polymer ratio was 1:1 (w/w). These experiments utilized various ratios of acetone and methyl ethyl ketone, from 100% acetone to 0% acetone (or 100% methyl ethyl ketone). Ratios, as measured by the weight of each individual solvent measured to add to the mixture of solvents, of 90:10, 1:2, and 2:1 were also investigated. In some experiments, the drug coated stents were tested for the cumulative drug release at 24 hours without having been sterilized. In other experiments, some stents were sterilized with electron-beam irradiation at 25 KGy (two passes of 12.5 KGy) dose and then the cumulative drug release was evaluated. Each data point represents the cumulative release for at least n=3 stents. The cumulative release at 24 hours on the abscissa versus the volume percent acetone in the coating solvent on the ordinate is illustrated in FIG. 4. As illustrated in FIG. 4, there is a linear relationship between the percent of everolimus released at 24 hours and the percent acetone in the coating solvent. The correlation coefficient, $R^2$, for the non-sterilized stents is about 0.952, while the value for the sterilized stents is about 0.951.

While particular embodiments of the present invention have been shown and described, it will be obvious to those skilled in the art that changes and modifications can be made without departing from this invention in its broader aspects. Therefore, the claims are to encompass within their scope all such changes and modifications as fall within the true spirit and scope of this invention.

What is claimed:
1. A method for modulation of hydrophobic drug release from a coating, the method comprising:
  providing an amorphous or semi-crystalline hydrophobic polymer that has a glass transition temperature greater than 37° C.;
  providing a hydrophobic drug;
  providing a coating solvent comprising 10% to 90% acetone and 90% to 10% of a second solvent selected from the group consisting of methyl ethyl ketone, methyl isobutyl ketone and dimethylacetamide wherein % refers to weight %;
  dissolving the drug and the polymer in the coating solvent at a drug:polymer mass ratio of 1:1 to 1:3 to form a coating solution;
  spraying the coating solution onto a substrate;
  removing the solvent; and
  modulating the release rate of the drug from the coating formed after the solvent is removed by repeating the above operations of providing an amorphous or semi-crystalline hydrophobic polymer, providing a hydrophobic drug, providing a coating solvent, dissolving the drug and the polymer in the coating solvent, spraying the coating solution onto a substrate and removing the solvent, on at least one more occasion using the same polymer, drug, and drug to polymer mass ratio, using the same type of substrate wherein the substrate used is a substrate to which the coating solution of the polymer and the drug has not been applied, and using a different coating solvent which differs from the coating solvent used in the immediately previous execution of the operations in the choice of the second solvent, the ratio of acetone to the second solvent, or both the choice of the second solvent and the ratio of acetone to the second solvent.

2. The method of claim 1, wherein the coating solvent, one or more of the different coating solvents, or any combination thereof comprises 20% to 80% acetone and 80% to 20% of the second solvent.

3. The method of claim 1, wherein the substrate is an implantable medical device.

4. The method of claim 3, wherein the implantable medical device is a stent.

5. The method of claim 4, wherein the second solvent of the coating solvent, one or more of the different coating solvents, or any combination thereof is methyl ethyl ketone.

6. The method of claim 5, wherein the polymer is selected from the group consisting of poly(D,L-lactide), poly(L-lactide), poly(D,L-lactide-co-glycolide), poly(L-lactide-co-D, L-lactide), poly(L-lactide-co-glycolide) and combinations thereof.

7. The method of claim 6, wherein the drug is selected from the group consisting of rapamycin, 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin, everolimus, biolimus A9, deforolimus, tacrolimus, zotarolimus, pimecrolimus, temsirolimus, and combinations thereof.

8. The method of claim 7, wherein the drug is everolimus.

9. The method of claim 7, wherein the drug is zotarolimus.

10. The method of claim 8, wherein the stent further comprises a primer coating comprising 75/25 poly(D,L-lactide-co-glycolide).

11. The method of claim 9, wherein the stent further comprises a primer coating comprising 75/25 poly(D,L-lactide-co-glycolide).

12. The method of claim 4, wherein the coating thickness of any one or more of the coatings formed is less than about 50 µm.

13. The method of claim 2, wherein the substrate is a stent.

14. A method for modulation of hydrophobic drug release from a coating, comprising:
  providing an amorphous or semi-crystalline hydrophobic polymer that has a glass transition temperature greater than 37° C.;
  providing a hydrophobic drug;
  providing a first solvent that is a good solvent for both the polymer and the drug and has a boiling point less than or equal to 60° C.;

dissolving the drug and the polymer in the first solvent at a drug:polymer mass ratio of about 1:1 to about 1:3 to form a first coating solution;

spraying the first coating solution onto a substrate to form a first coating;

determining the percent release of drug from the first coating over a selected time period;

providing a second solvent that is a good solvent for both the polymer and the drug and has a boiling point that is at least 10° C. higher than the boiling point of the first solvent;

dissolving the drug and the polymer in the second solvent at the same drug: polymer ratio as that selected for the first solvent to form a second coating solution;

spraying the second coating solution onto another substrate to form a second coating;

determining the percent release of drug from the second coating over the same time period as that selected for release from the first coating;

preparing a graph with percent drug release as the abscissa and percent of first solvent as the ordinate;

plotting the percent release at 100% first solvent and the percent release at 0% first solvent (100% second solvent) wherein % refers to weight %;

drawing a straight line between the two plotted points;

selecting a desired percent release over the selected time period between the percent release at 100% first solvent and the percent release at 0% first solvent, including the end points; and determining the percent first and second solvent from the graph using the selected percent release.

15. The method of claim 14, wherein the first solvent is acetone.

16. The method of claim 14, wherein the second solvent is selected from the group consisting of methyl ethyl ketone, methyl isobutyl ketone, and dimethylacetamide.

17. The method of claim 14, wherein the second solvent is methyl ethyl ketone.

18. The method of claim 14, wherein the substrate is an implantable medical device.

19. The method of claim 18, wherein the implantable medical device is a stent.

20. The method of claim 14, wherein the polymer is selected from the group consisting of poly(D,L-lactide), poly(L-lactide), poly(D,L-lactide-co-glycolide), poly(L-lactide-co-D,L-lactide), poly(L-lactide-co-glycolide) and combinations thereof.

21. The method of claim 14, wherein the drug is selected from the group consisting of everolimus, zotarolimus, and combinations thereof.

22. The method of claim 14, wherein the polymer is selected from the group consisting of poly(D,L-lactide-co-glycolide), poly(L-lactide-co-glycolide), and combinations thereof.

23. The method of claim 1, wherein the polymer is selected from the group consisting of poly(D,L-lactide-co-glycolide), poly(L-lactide-co-glycolide), and combinations thereof.

* * * * *

UNITED STATES PATENT AND TRADEMARK OFFICE
CERTIFICATE OF CORRECTION

| | | |
|---|---|---|
| PATENT NO. | : 8,562,669 B2 | Page 1 of 1 |
| APPLICATION NO. | : 12/147442 | |
| DATED | : October 22, 2013 | |
| INVENTOR(S) | : Pacetti et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1337 days.

Signed and Sealed this
Seventh Day of April, 2015

Michelle K. Lee
*Director of the United States Patent and Trademark Office*